United States Patent
Batlaw et al.

(10) Patent No.: US 6,452,020 B1
(45) Date of Patent: Sep. 17, 2002

(54) METHODS OF MAKING MAGENTA COLORANTS FOR INK SYSTEMS

(75) Inventors: Rajnish Batlaw, Spartanburg, SC (US); Patrick D. Moore, Pacolet, SC (US)

(73) Assignee: Milliken & Company, Spartanburg, SC (US)

( * ) Notice: Subject to any disclaimer, the term of this patent is extended or adjusted under 35 U.S.C. 154(b) by 0 days.

(21) Appl. No.: 09/832,054

(22) Filed: Apr. 10, 2001

(51) Int. Cl.7 ............................................. C07D 311/88
(52) U.S. Cl. ...................................... 549/225; 549/226
(58) Field of Search ................................. 549/226, 225

(56) References Cited

U.S. PATENT DOCUMENTS

| | | | |
|---|---|---|---|
| 3,873,573 A | 3/1975 | Farber et al. ............ | 260/343.4 |
| 4,330,473 A | 5/1982 | Hatano et al. ............... | 549/226 |
| 4,806,657 A | 2/1989 | Zink ........................... | 549/226 |
| 4,833,197 A | 5/1989 | Schelhaas et al. .......... | 524/594 |
| 5,250,708 A | 10/1993 | Barry, Jr. .................... | 549/226 |
| 5,919,839 A | 7/1999 | Titterington et al. ........ | 523/161 |
| 5,919,846 A | 7/1999 | Batlaw et al. ................ | 524/83 |
| 6,040,482 A | 3/2000 | Harris et al. ................ | 564/443 |

*Primary Examiner*—Alan L. Rotman
*Assistant Examiner*—Raymond Covington
(74) *Attorney, Agent, or Firm*—Terry T. Moyer; William S. Parks

(57) ABSTRACT

Novel addition products of isocyanates with oxyalkylene-substituted aminophenol compounds as intermediates for the production of urethane-substituted xanthene colorants, particularly triphenylmethane derivatives such as rhodamines, are provided. The xanthene colorants exhibit improved wax and/or oil solubility and high purity. The urethane-substituted xanthene colorant features very good wax and/or oil solubility, and is believed to be relatively nontoxic. A method for producing this novel colorant is also provided.

6 Claims, No Drawings

METHODS OF MAKING MAGENTA COLORANTS FOR INK SYSTEMS

FIELD OF THE INVENTION

This invention relates to novel addition products of isocyanates with oxyalkylene-substituted aminophenol compounds as intermediates for the production of urethane-substituted xanthene colorants, particularly triphenylmethane derivatives such as rhodamines. The xanthene colorants exhibit improved wax and/or oil solubility and high purity. The urethane-substituted xanthene colorant features very good wax and/or oil solubility, and is believed to be relatively nontoxic. A method for producing this novel colorant is also provided.

BACKGROUND OF THE PRIOR ART

All U.S. and foreign patents cited within this specification are hereby incorporated by reference.

Xanthene dyes, and in particular rhodamine dyes, are well known in the art as exemplified in the COLOUR INDEX, 3rd. ed., Vol. 4, pp. 4419–4422 (1971). These dyes range from bright red to bright bluish red, and typically fluoresce orange or red upon exposure to ultraviolet light. Most importantly, such rhodamines provide magenta colorations for various coloring systems. Rhodamine dyes are useful in a variety of applications including coloring soaps and other cleaning products, water tracing and leak detection. While such dyes have been utilized within certain portions of the colorant industry, their use has been limited due to toxicity issues. Thus, they are generally unsuitable for use when human exposure to such a dye is likely. Less toxic rhodamines have been developers such as Rhodamine WT, available from Abbey Color Products. However, such a low-toxicity rhodamine exhibits relatively poor light fastness, as well as poor solubility in non polar media.

Another category of available xanthene dyes for colorant uses, particularly triphenylmethane type-xanthenes, is exemplified by the fluoran compounds disclosed in Farber et al., U.S. Pat. No. 3,873,573; Hatano et al., U.S. Pat. No. 4,330,473; and Zink, U.S. Pat. No. 4,806,657. The compounds are diamino-xanthene dyes having amino groups in the 3- and 7-positions, including phenyl-substituted amino groups. These patents also disclose p-methoxy-N-phenylaniline intermediates which may be reacted with a ketonic acid. Such dyes are particularly useful as recording material, since the lactone ring within these xanthene compounds are susceptible to opening thereby converting the faintly colored material to a dark green or black color.

Typical prior art processes for manufacturing rhodamine dyes provide for condensing m-dialkylaminophenol with phthalic anhydride. In synthesizing a poly(oxyalkylene) substituted colorant, it is desirable to alkoxylate one or more of the reactants or intermediates which form the colorant. However, the intermediates used in a typical rhodamine synthesis may not be readily alkoxylated without adding poly(oxylakylene) to sites on the intermediate which participate in colorant formation. U.S. Pat. No. 5,250,708 teaches us of a process to produce a specific oxyalkylene substituted aminophenol intermediate that is successfully used in the production of poly(oxyalkylene)-substituted xanthene colorant. U.S. Pat. Nos. 5,919,846, 5,919,839, and PCT patent Application WO 94/14902 describes the reaction of hydroxyl containing colorants with mono and diisocyanates.

More versatile xanthene colorants have been produced for ink applications. Such xanthenes include those taught within U.S. Pat. No. 5,250,708 which teaches a method of producing a poly(oxyalkylene) xanthene colorant by reacting 2-(4-N,N-diethylamine-2-hydroxy benzoyl) benzoic acid with 3-methoxy-N,N-di(polyoxyalkylene oxide) aniline. The benzoic acid intermediate is produced in a reversible reaction from N,N-diethyl-m-aminophenol and phthalic anhydride. Since some residual diethyl-m-aminophenol may be present during this subsequent reaction, the intermediate may react with the N,N-diethyl-m-aninophenol to form the xanthene dyestuff. U.S. Pat. No. 6,040,482 improves upon this approach by providing a novel intermediate which does not form a xanthene dyestuff upon reaction with phthalic anhydride. Furthermore, the invention provides an oxyalkylenated xanthene, the physical and chemical properties of which can be easily modified through subsequent reaction of the free hydroxyl groups with electrophiles such as anhydrides, isocyanates, esters, acid chlorides, and the like. However, the reaction of these electrophiles is limited to the availability of the free hydroxyl groups in the oxyalkylenated xanthene, as some of the hydroxyl groups react with the phthalic anhydride to form phthalates during the formation of the xanthene colorant. These phthalates tend to act as impurities with its own unique solubility characteristics. Examples of polyoxyalkylene substituted colorants include those taught within U.S. Pat. No. 5,919,839, and EP 0 896 038 A2 describe phase change, or hot melt inks utilizing the reaction product of an isocyanate (e.g., octadecyl isocyanate) and hydroxyl containing colorant to form a colored urethane wax. These colorants, in order to be utilized within such hot melt ink systems require high purity and complete compatibility within the wax-based ink system. The presence of phthalates, however, in these urethane substituted xanthene colorants reduces the compatibility of these colorants in such wax based ink systems. U.S. Pat. No. 4,833,197 describes an offset ink using diluents, for example, mineral oils with a boiling range of 200°–350° C., and no more than 20% of aromatic components. Again, however, phthalates present within the urethane substituted xanthene colorants remain insoluble in these diluents, thus making these colorants unsuitable for use in these applications.

Thus, even though poly(oxyalkylenated) xanthene colorants have only recently been made available to the colorant market, the utilization of such colorants, particularly made from the intermediate disclosed within the '482 patent, the use of such colorants has still been limited due to the lack of complete compatibility in wax and/or oil based systems due to the formation of the aforementioned deleterous phthalates (through the reaction of phthalic anhydride on the free hydroxyls groups of the polyoxyalkylene moieties). There thus exists a need to improve upon this procedure and ultimately to produce a novel intermediate which provides the ability of forming highly desirable derivitized oxyalkylenated xanthene colorants but does not require a multi-step process in forming the intermediate alone which furthermore precludes the formation of deleterious phthalates. To date, the prior art has not accorded such an improvement within this specific area of colorant chemistry. Because of this lack of such a specific type of colorant, the versatility and widespread use of such colorants in different types of inks and substrate has not been accomplished. There is thus a need to provide wax-based inkjet colorants and compositions which are readily and consistently soluble due to reduction of phthalation products. To date, there have been no improvements for xanthene colorants reducing the possible production of deleterious phthalate impurities thus permitting consistent use within, as one possible end-use, wax-based ink-jet inks.

OBJECTS OF THE INVENTION

Therefore, one of the objects of the invention is to provide a urethane-substituted xanthene colorant. Another object of this invention is to provide a synthetic route for a xanthene colorant wherein all reactants are substituted with urethane groups. Another object of the invention is to provide a specific urethane substituted aminophenol intermediate for the production of a urethane substituted xanthene colorant. Still another object of the invention is to provide an intermediate that is an addition product of poly(oxyalkylene) aminophenol and an isocyanate for use in the manufacture of xanthene colorants, particularly rhodamine colorants. A further object of the invention is to provide an addition product of an isocyanate with a specific propoxylated aminophenol intermediate which will alternatively form a xanthene dyestuff upon reaction with phthalic anhydride and thus provides excellent yield of the desired colorant alone. Yet another object of this invention is to provide a relatively inexpensive method for producing such beneficial urethane substituted xanthene (or other type) colorants.

Accordingly, this invention encompasses an aminophenol derivative intermediate comprising at most a total of three moles of a constituent selected from the group of oxyalkylene groups having from 3 to 12 carbon atoms, alkoxy alkylester groups having from 3 to 12 carbon atoms, glycidol, and a glycidyl group wherein said constituent is solely bonded to the amine, and wherein of all of the hydroxyl moieties present on said intermediate, at least one is isocyanate-capped and thus forms a urethane moiety.

Thus, the compound noted above with at least two urethane groups present on the hydroxyls, as well as at least three urethanes likewise present are preferred as well. Most preferably, at least three urethane groups are present, and such such a preferred specific compound encompassed within this invention is an intermediate conforming to the structure of Formula (I)

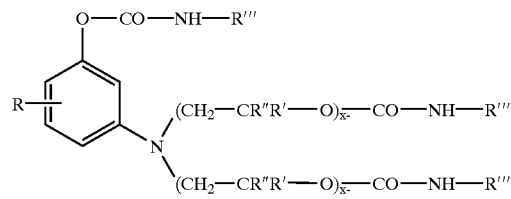

wherein x+y is greater than 0 and less than 4; wherein R is selected from the group consisting of hydrogen, halo, formyl, $C_1$–$C_{20}$ alkoxy, and $C_1$–$C_{20}$ alkyl; wherein R' is selected from the group consisting of $C_1$–$C_{10}$ alkoxy, $C_1$–$C_{10}$ polyoxyalkoxy, $C_1$–$C_{10}$ alkylester, and $C_1$–$C_{10}$ alkyl; wherein R" is selected from the group consisting of hydrogen and $C_1$–$C_4$ alkyl groups; and wherein R''' is selected from the group selected from hydrogen, $C_1$–$C_{24}$ alkyl groups, $C_1$–$C_{24}$ alkoxy groups, and $C_1$–$C_{24}$ ester groups. Preferably R is H, methyl, ethyl, Cl, Br or I, R" is hydrogen, methyl, or ethyl, and R''' is hydrogen, methyl, or ethyl. In a more preferred embodiment, the N,N-bisurethane-m-aminophenol intermediate is substituted with methyl or ethyl, or is unsubstituted, i.e. R is H. The intermediate is prepared from m-aminophenol or p-aminophenol which is reacted with at most a total of three moles of a constituent selected from the group of oxyalkylenes having from 3 to 12 carbon atoms, alkoxyalkylesters having from 3 to 12 carbon atoms, glycidol, and a glycidyl group wherein said constituent is solely bonded to the amine, and R''' is selected from $C_1$–$C_4$ alkyl.

Furthermore, the inventive colorant preferably conforms with the structure of Formula (II)

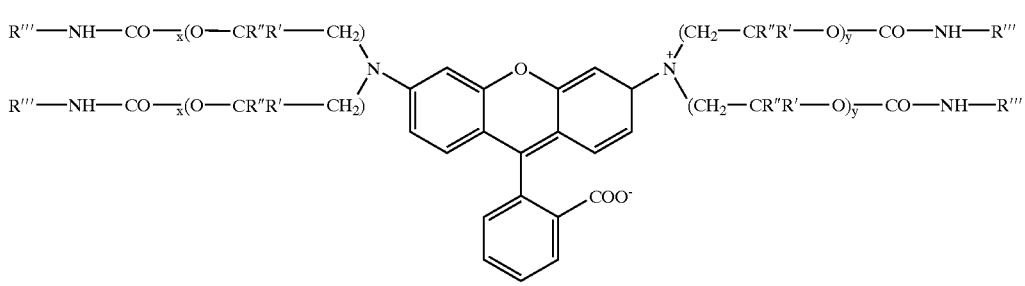

Since the oxyalkylene groups as noted above, as well as the phenol group (and any others present on the ring, potentially) are reactive, the reaction with a certain amount of isocyanate (such as, without limitation, octadecyl isocyanate) produces the desired urethane moieties thereon. It appears that the hydroxyls on the oxyalkylene, etc., groups react more readily with such isocyanates; thus, a lower molar ratio of isocyanate reacted with the base oxyalkyenated aminophenol should first produce urethanes on the oxyalkylene moieties with the phenol hydroxyl reacting more readily as greater amounts of isocyanate are added.

wherein x+y is greater than 0 and less than 4; wherein R is selected from the group consisting of hydrogen, halo, formyl, $C_1$–$C_{20}$ alkoxy, and $C_1$–$C_{20}$ alkyl; wherein R' is selected from the group consisting of $C_1$–$C_{10}$ alkoxy, $C_1$–$C_{10}$ polyoxyalkoxy, $C_1$–$C_{10}$ alkylester, and $C_1$–$C_{10}$ alkyl; wherein R" is selected from the group consisting of hydrogen and $C_1$–$C_4$ alkyl groups; and wherein R''' is selected from the group selected from hydrogen and $C_1$–$C_{24}$ alkyl groups; or any salts thereof (such as salts with inorganic or organic anions, including, without limitation, halides, sulfonates, hydrogen sulfonates, methylsulfates, and the like). Such an aminophenol intermediate in Formula (I) is useful in producing the xanthene colorant of Formula (II).

DETAILED DESCRIPTION OF THE INVENTION

The amino group of said aminophenol is di-substituted with an addition product of an isocyanate and a poly (oxyalkylene) substituent having a straight or branched polymer chain selected from oxyalkylene oxide, oxyalkylester and glycidol. In one embodiment, at least one mole of the urethane-substituted m-aminophenol is reacted with phthalic anhydride or other aromatic compound having an aldehyde functionality available. A second mole of urethane substituted m-aminophenol may also be provided to form a rhodamine colorant. The invention herein also provides for synthesis of a black, or dark green, xanthene colorant using one mole of N,N-bisurethane-p-aminophenol with one mole of a polymeric or non-polymeric p-aminophenol. This novel intermediate has the advantage being useful in the traditional route of xanthene synthesis, i.e., the condensation reaction of an aminophenol and phthalic anhydride.

In particular, it is highly desirable to provide a method of forming an addition product of an isocyanate with a specific propoxylated aminophenol intermediate of U.S. Pat. No. 6,040,482. Furthermore, the aminophenol intermediate encompassed within this invention thus comprises at most a total of three moles of a constituent selected from the group of oxyalkylene groups having from 3 to 12 carbon atoms, alkoxy alkylester groups having from 3 to 12 carbon atoms, glycidol, and a glycidyl group wherein said constituent is solely bonded to the amine, and the free hydroxyl is reacted with an isocyanate such as octadecyl isocyanate. Such a method of producing the addition product of an isocyanate with such a specific oxyalkylenated aminophenol intermediate is also contemplated within this invention as well. The amine constituent may reside in any position relative to the phenol on the benzene ring (i.e., p-aminophenol, o-aminophenol, or m-aminophenol); however, m-aminophenol is preferred. Thus, the preferred m-aminophenol intermediate is also contemplated within this invention as is the method of making such a compound, as defined by the Figure (I)

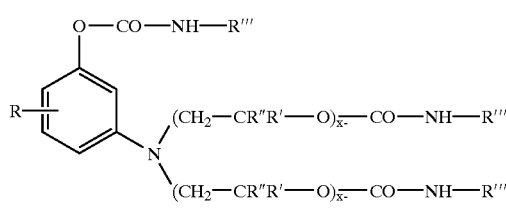

(I)

wherein x+y is greater than 0 and less than 4; wherein R is selected from the group consisting of hydrogen, halo, formyl, $C_1$–$C_{20}$ alkoxy, and $C_1$–$C_{20}$ alkyl; wherein R' is selected from the group consisting of $C_1$–$C_{10}$ alkoxy, $C_1$–$C_{10}$ polyoxyalkoxy, $C_1$–$C_{10}$ alkylester, and $C_1$–$C_{10}$ alkyl; and wherein R" is selected from the group consisting of hydrogen and $C_1$–$C_4$ alkyl groups; and wherein R'" is selected from the group selected from hydrogen, $C_1$–$C_{24}$ alkyl groups, $C_1$–$C_{24}$ alkoxy groups, and $C_1$–$C_{24}$ ester groups. Such a method comprises the reaction of at most 3 moles of a compound selected from the group consisting of an alkylene oxide having from 3 to 10 carbon atoms and glycidol with a m-aminophenol compound of the Formula (II) wherein R is selected from the group consisting of hydrogen, halo, $C_1$–$C_{20}$ alkoxy and $C_1$–$C_{20}$ alkyl at a reaction temperature of from about 120 to about 250° F. The invention also covers the actual compound of Formula (I), above as well. Preferably R above (for both I and II) is hydrogen, $C_{1-4}$ alkoxy, or $C_{1-4}$ alkyl; most preferably R' is hydrogen. Also, preferably R" is methyl or ethyl (most preferably methyl), and R" is preferably H. R'" is selected from the group consisting of $C_1$–$C_{24}$ alkyl, preferably R" is $C_{12}$–$C_{24}$ alkyl, most preferably R" is $C_{18}$.

It is an advantage of the present invention that the urethane substituted xanthene can be design engineered to obtain desired properties for specific printing platforms and architectures. It is also an advantage of the present invention that the urethane substituted xanthene is very pure, being free of salts and other insoluble contaminants. It is another advantage of the present invention that the urethane substituted xanthene can be used in combination with other phase change ink carrier materials to obtain ink compositions that possess excellent spectral strengths. It is still another advantage of the present invention that the urethane substituted xanthene are substantially transparent. It is yet another advantage of the present invention that the urethane substituted xanthene provide close to true magenta shades with low hue error and grayness. These and other aspects, features and advantages are obtained by the use of urethane substituted xanthenes that are the reaction products of urethane substituted aminophenol with phthalic anhydride that are suitable for use with waxes and/or oils in phase change ink jet inks and offset inks that may be employed in direct or indirect printing applications.

It has been found that even though the reaction of isocyanates with oxyalkylenated aminophenol compounds results in the formation of oxyalkylene groups on the phenolic hydroxyl group, the subsequent reaction of the urethane substituted aminophenol with phthalic anhydride proceeds very well producing a xanthene colorant free of phthalates, pure and completely compatible in wax and/or oil systems conforming with the Formula (II)

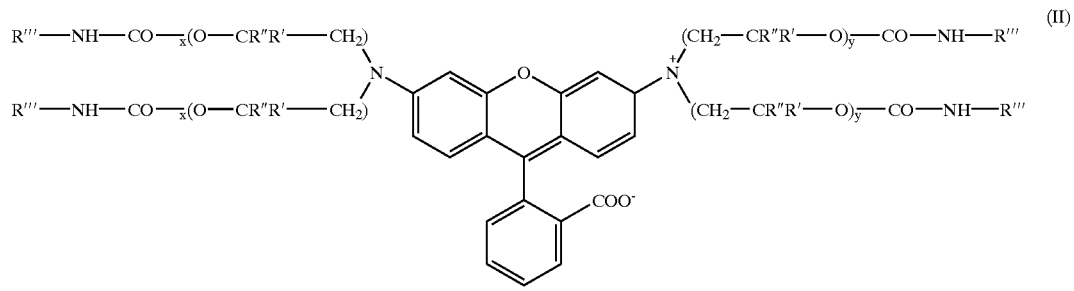

(II)

wherein x+y is greater than 0 and less than 4; wherein R is selected from the group consisting of hydrogen, halo, formyl, $C_1$–$C_{20}$ alkoxy, and $C_1$–$C_{20}$ alkyl; wherein R' is selected from the group consisting of $C_1$–$C_{10}$ alkoxy, $C_1$–$C_{10}$ polyoxyalkoxy, $C_1$–$C_{10}$ alkylester, and $C_1$–$C_{10}$ alkyl; and wherein R" is selected from the group consisting of hydrogen and $C_1$–$C_4$ alkyl groups; and wherein R'" is selected from the group selected from hydrogen and $C_{24}$ alkyl groups; or any salts thereof.

The standard reactions followed in the past to attach oxyalkylene groups to amino or hydroxyl pendant groups have included reactions with ethylene oxide without any base present. The resultant reactions thus quickly drive the addition of the oxyalkylene groups to the undesired phenolic hydroxyl sites, and ends up preventing the desired reaction with phthalic anhydride to form a xanthene. In the inventive method, the urethane linkage, presumably, breaks in a reversible reaction, thus allowing the reaction with phthalic anhydride to proceed and form the xanthene colorant. This reaction appears to work with any aminophenol compound, although highly preferred is a m-aminophenol base compound with extra pendant groups selected from the group consisting of hydrogen, halo, $C_1$–$C_{20}$ alkoxy, and $C_1$–$C_{20}$ alkyl. Again, in each instance, the 1 to 3 moles of, for instance, propylene oxide (per m-aminophenol compound) when directly reacted with the starting aminophenol reactant at a suitable relatively low temperature, will only attack the amino groups, thereby producing an oxypropyl-substituted aminophenol having at most an average of 1.5 monomers (i.e., 2 monomers on one site and 1 monomer on the other) of propylene oxide added per carbon-nitrogen bond of the amino moiety. Such an intermediate is represented by Formula (I), above, and can thus be reacted with at least one other reactant compound to form any number of different colorants. For instance, this intermediate may also be reacted benzaldehyde (preferably one with carboxylic or sulfonate groups attached, such as benzaldehyde-2,4-disulfonic acid), as taught within the Barry, Jr. patent., as well as through the reaction of other compounds, such as, as merely an example, o-formyl-benzenesulfonic acid. Furthermore, the inventive intermediate will not alternatively form the correlative xanthene dyestuff during the reaction with phthalic anhydride. Such a dyestuff is highly regulated and poses potential toxicity problems and thus it is desirable to avoid production of such a compound. Furthermore, the dyestuff cannot be modified physically and/or chemically since there are no remaining reactive sites at which electrophilic groups may be attached. The inventive method and the inventive intermediate therefore provide clear distinct advantages over the previously disclosed xanthene compounds production methods. Additionally, the inventive intermediate can be reacted with other reactant compounds to form other types of colorants. For example, an oxazine colorant may be formed by nitrosating one mole of the inventive intermediate and subsequently reacting that reactant compound with a second mole of the inventive intermediate. Furthermore, other colorants may also be formed, such as coumarins, through the reaction of the inventive intermediate with other reactant compounds such as, without limitation, ethylcyanoacetate and phenylenediamine.

As noted above such novel intermediates permit production of colorants made therefrom (particularly xanthenes) that are substantially phthalate-free through the initial reaction of the isocyanate constituent with the free hydroxyls during reaction with phthalic anhydride. A low amount of phthalate may be produced on the final colorant product; however, such an amount is drastically reduced in comparison with the previously followed production methods without isocyanate-capped hydroxyl moieties. Thus, the amount of phthalate produced by the inventive method and thus found on the target xanthene colorant is below about five (5) molar percent in total. Such an amount is thus the definition of the term "substantially phthalate-free" as well.

Such inventive substantially phthalate-free colorants may be utilized in any number of coloring procedures, including ink, paint, print, dye, tint, and the like, applications. Thus, compositions utilized to provide colorations to various substrates, including, without limitation, cellulose-based substrates (paper, cotton fabrics, and the like), magazine-paper substrates, and the like, are preferred surfaces for coloring. Other surfaces, substrates, etc., may be contacted with the inventive colorants as well. Most preferably, however, such colorants are to be utilized in ink applications, most notably inkjet, lithographic, and offset ink operations. Offset applications are basically newsprint, magazine-print, and like types, of printing procedures. In such operations, it is important to provide long-term stability of the target ink solution solubility of the colorant in the ink compositions and water resistance of the printed image from the ink composition. For inkjet inks, particularly wax-based types, heat stability of the entire ink system is of paramount importance, since the printing process comprises numerous periods of heating and cooling cycles in order for the inks to perform the desired print operation. Thus, such inks must be able to retain their color strength upon evaluation of exposure at 150° C. for prolonged and/or intermittent periods (e.g., 30 minutes or 5 minutes heated, 5 minutes cooled, 5 minutes heated, and so on, as merely examples). The color difference between an initial print and an oven-aged print is calculated using the following equation:

$$\Delta E^* = ((L^*\text{initial} - L^*\text{aged})^2 + (a^*\text{initial} - a^*\text{aged})^2 + (b^*\text{initial} - b^*\text{aged})^2)^{1/2}$$

wherein $\Delta E^*$ represents the difference in color between the initial printed sample and the sample printed with oven aged ink. $L^*$, $a^*$, and $b^*$ are the color coordinates; wherein $L^*$ is a measure of the lightness and darkness of the print sample; $a^*$ is a measure of the redness or greenness of the print sample; and $b^*$ is a measure of the yellowness or blueness of the print sample. For a further discussion and explanation of this testing procedure, see Billmeyer, F. W., et al., *Principles of Color Technology,* 2nd Edition, pp. 62–64 and 101–04. Thus, the inks must exhibit a minimal change in color over such time (e.g., $\Delta E^*$ of at most 1.5).

For offset inks, and particularly heat set types, generally, such compositions include alkyds as heat-set inks used primarily as pigment-wetting vehicles (although they may also improve the stability of the ink, improve the gloss of the ink on the target substrate, and affect water pick-up after contact with the desired surface). High boiling petroleum distillates are utilized as the diluent/solvent components therein within such heat-set offset ink formulations. Other additives commonly found within such offset inks are polyethylene (slip agent), organic aluminum compounds (rheology modifiers), and low molecular weight micronized hydrocarbon resins (to increase ink tack).

For lithographic inks (cold set), generally, such compositions function through penetration of the ink within the target substrate (e.g., paper, for example). Mineral oil or vegetable oils are utilized as carriers within such compositions with small amounts of varnish (typically gilsonite or hydrocarbon-based resins, as examples) added to control the lithographic properties of the ink composition, with components such as bentonite, for example, added for rheology control.

Wax-based inkjet inks are generally solid at room temperature and subsequently heated to a temperature above its melting point and maintained at a temperature above about 150° C. wherein the composition must exhibit fluid physical properties required for inkjet printing methods. Thus, these inkjet ink composition generally comprise two component types: colorants and vehicles for the colorants. The vehicle often consists of a blend of polymers which function to control the viscosity temperature profile and balance the performance of the ink in the printhead with the performance of the ink on the target substrate surface (e.g., again, paper). Such polymers tend to be based upon fatty acids, urethanes, and natural and/or synthetic waxes.

DESCRIPTION OF THE PREFERRED EMBODIMENTS

Without limiting the scope of the invention, the preferred features of the invention are hereinafter set forth.

Intermediate Synthesis

EXAMPLE 1

193 parts of the polyoxyalkylene substituted aminophenol intermediate precursor of Formula (A)

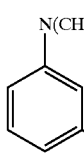

(A)

N(CH$_2$—CH(CH$_3$)—OH)$_2$

OH (from U.S. Pat. No. 5,250,708) were charged into a reactor vessel with 500 parts of octadecenyl isocyanate, and 13.4 parts of dibutyltindilaurate catalyst. The mixture was heated with stirring to 70° C. under a N$_2$ atmosphere. After 4.0 hours at 70 C. an FT-IR spectrum of the product was obtained to insure all isocyanate functionality is consumed. The absence (disappearance) of a peak at about 2275 cm$^{-1}$ (NCO) and the appearance (or increase in magnitude) of peaks at about 1740–1680 cm$^{-1}$ and about 1540–1530 cm$^{-1}$ corresponding to urethane frequencies, thereby confirm the conversion of the isocyanate to the urethane.

EXAMPLE 2

193 parts of the polyoxyalkylene substituted aminophenol intermediate precursor of Formula (A)

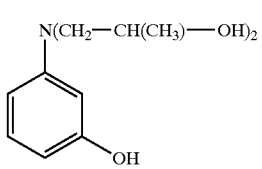

(A)

N(CH$_2$—CH(CH$_3$)—OH)$_2$

OH (from U.S. Pat. No. 5,250,708) were charged into a reactor vessel 168 parts of n-butyl isocyanate, and 13.4 parts of dibutyltindilaurate catalyst. The mixture was heated with stirring to 70° C. under a N$_2$ atmosphere. After 4.0 hours at 70 C. an FT-IR spectrum of the product was obtained to insure all isocyanate functionality is consumed. The absence (disappearance) of a peak at about 2275 cm$^{-1}$ (NCO) and the appearance (or increase in magnitude) of peaks at about 1740–1680 cm$^{-1}$ and about 1540–1530 cm$^{-1}$ corresponding to urethane frequencies, thereby confirm the conversion of the isocyanate to the urethane.

Colorant Production

The general methods of making the preferred inventive colorants are as follows:

EXAMPLE 3

(Xanthene)

700 parts of the intermediate produced in Example-1 was charged into a flask containing 399 parts of phthalic anhydride, 41.6 parts of 93% sulfuric acid, and 832 parts of toluene (solvent). The reactants were then heated up to 100° C. and maintained at a temperature from about 100 to 105° C., until the 340 nm peak, representing the inventive intermediate, in the uv/vis spectrum has disappeared and the color value, measured as absorbance (550 nm) per gramn per liter, representing the target xanthene colorant stops to increase in magnitude (through measurement by a uv/vis spectrophotometer). The product was washed with deionized water and filtered and the toluene was removed by the azeatrope with water to yield the urethane substituted xanthene, leaving a compound exhibiting a brilliant magenta hue and represented by Formula (11)

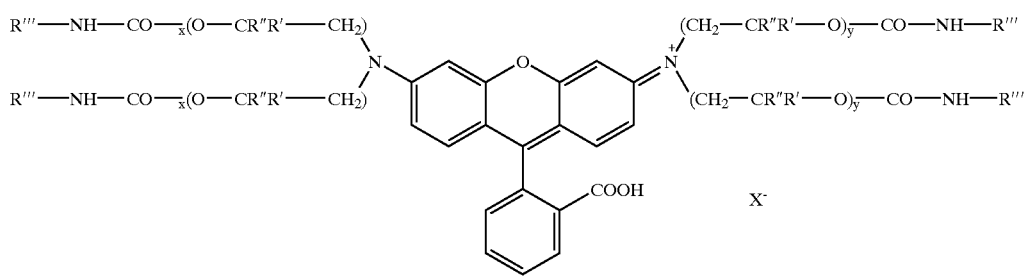

(II)

wherein R''' is octadecenyl, R'' is methyl, R' is hydrogen, X is HSO$_4^-$, and x=y=1 (thus x+y=2.

Ink Applications

EXAMPLE 4

(Wax Based Inks)

20 parts of the xanthene colorant produced in Example 3 was mixed with a color stick from Xerox for a Phaser 850 printer under heat (120–150° C.). The product was allowed to mix well while hot and poured into an aluminum dish. This mixture was subjected to several heating and cooling cycles to determine compatibility through these cycles. The product appeared to be completely compatible with the wax systems throughout the heating/cooling cycles. After contacting with paper, the colorant exhibiting ΔE* well below 1.5 in accordance with the oven aging test described above.

EXAMPLE 5
(Offset Based Inks)

20 parts of the xanthene colorant produced in Example 3 was mixed with a 56 parts of heatset varnish LV-3768 from Lawter Chemical, and 24 parts of Magiesol 47 from Magie Brothers. The product was completely compatible. The final mixture was used as an ink and drawn down on paper. The image on paper is a brilliant red and indicated that the individual components of the ink were completely compatibility. The ink was stable over a period of at least 6 weeks (with a resultant ΔE* well below 1.5 as determined by the oven aging test described above).

EXAMPLE 6
(Comparative)

193 parts of polyoxyalkylene substituted aminophenol intermediate precursor of Formula (A)

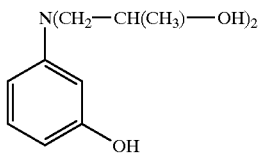

(A)

(from U.S. Pat. No. 5,250,708) were charged into a reactor vessel with 403 parts of phthalic anhydride, 6 parts of 1-methylimidazole catalyst and 200 parts of toluene (solvent). The mixture was heated with stirring to 120 C. for 72 hours until the 340 nm peak, representing the inventive intermediate, in the uv/vis spectrum has disappeared and the color value, measured as absorbance (550 nm) per gram per liter, representing the target xanthene colorant stops to increase in magnitude (through measurement by a uv/vis spectrophotometer). Once the color value had stopped to increase, the reaction was cooled down to 70 C., and 500 parts of octadecenyl isocyanate, and 13.4 parts of dibutyltindilaurate catalyst were charged to the reaction vessel. The mixture was heated with stirring to 70° C. under a $N_2$ atmosphere. After 4.0 hours at 70 C. an FT-IR spectrum of the product was obtained to insure all isocyanate functionality is consumed. The absence (disappearance) of a peak at about 2275 $cm^{-1}$ (NCO) and the appearance (or increase in magnitude of peaks at about 1740–1680 $cm^{-1}$ and about 1540–1530 $cm^{-1}$ corresponding to urethane frequencies, thereby con finn the conversion of the isocyanate to the urethane.

EXAMPLE 7
(Comparative)

20 parts of the xanthene colorant produced in Example 6 was mixed with a color stick from Xerox for a Phaser 850 printer under heat (120–150 C.). The product was allowed to mix well while hot and poured into an aluminum dish. This mixture was subjected to several heating and cooling cycles to determine compatibility through these cycles. The product appeared to show inhomogeneity and precipitation was visible over a period of time through the heating/cooling cycles (with a resultant ΔE* well above 1.5 after oven aging).

EXAMPLE 8
(Comparative)

20 parts of the xanthene colorant produced in Example 6 was mixed with a 56 parts of heatset varnish LV-3768 from Lawter Chemical, and 24 parts of Magiesol 47 from Magie Brothers. The product was not completely compatible. The final mixture was used as an ink and drawn down on paper. The image on paper is a brilliant red but indicated an inhomogeneous mixture with particle precipitation (with a resultant ΔE* well above 1.5 after oven aging).

There are, of course, many alternate embodiments and modifications of the present invention which are intended to be included within the spirit and scope of the following claims.

What is claimed is:

1. A method of producing a substantially phthalate-free xanthene colorant comprising the steps of (a) providing an aminophenol derivative intermediate comprising at most a total of three moles of a constituent selected from the group of oxyalkylene groups having from 3 to 12 carbon atoms, alkoxy alkylester groups having from 3 to 12 carbon atoms, glycidol, and a glycidyl group wherein said constituent is solely bonded to the amine, and wherein of all of the hydroxyl moieties present on said intermediate, at least one is isocyanate-capped and thus forms a urethane moiety; and (b) reacting said aminophenol derivative intermediate of step "a" with a phthalic anhydride-containing compound.

2. The method of claim 1 wherein of all of the hydroxyl moieties present on said intermediate of step "a", at least two are isocyanate-capped and thus form urethane moieties.

3. The method of claim 2 wherein of all of the hydroxyl moieties present on said intermediate of step "a", at least three are isocyanate-capped and thus form urethane moieties.

4. The method of claim 1 wherein said aminophenol derivative intermediate of step "a" conforms to the structure of Formula (I)

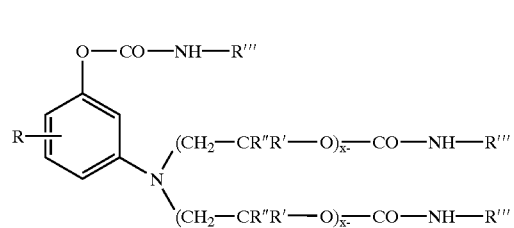

(I)

wherein x+y is greater than 0 and less than 4; wherein R is selected from the group consisting of hydrogen, halo, formyl, $C_1$–$C_{20}$ alkoxy, and $C_1$–$C_{20}$ alkyl; wherein R' is selected from the group consisting of $C_1$–$C_{10}$ alkoxy, $C_1$–$C_{10}$ polyoxyalkoxy, $C_1$–$C_{10}$ alkylester, and $C_1$–$C_{10}$ alkyl; and wherein R" is selected from the group consisting of hydrogen and $C_1$–$C_4$ alkyl groups; and wherein R''' is selected from the group selected from hydrogen, $C_1$–$C_{24}$ alkyl groups, $C_1$–$C_{24}$ alkoxy groups, and $C_1$–$C_{24}$ ester groups.

5. The method of claim 4 wherein R is selected from the group consisting of hydrogen, methyl, ethyl, Cl, Br, and I; wherein R" is selected from the group consisting of hydrogen, methyl, and ethyl; and wherein R''' is selected from the group consisting of hydrogen, methyl, and ethyl.

6. The method of claim 1 wherein said xanthene colorant conforms to the structure of Formula (II)

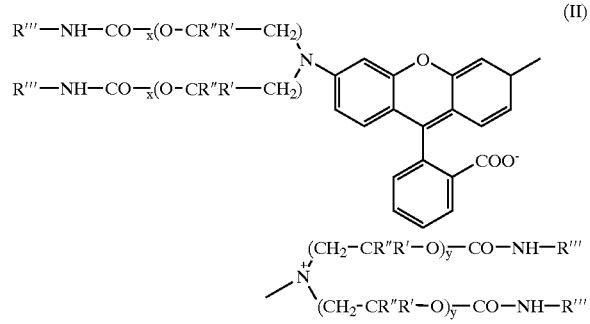

wherein x+y is greater than 0 and less than 4; wherein R is selected from the group consisting of hydrogen, halo, formyl, $C_1$–$C_{20}$ alkoxy, and $C_1$–$C_{20}$ alkyl; wherein R' is selected from the group consisting of $C_1$–$C_{10}$ alkoxy, $C_1$–$C_{10}$ polyoxyalkoxy, $C_1$–$C_{10}$ alkylester, and $C_1$–$C_{10}$ alkyl; and wherein R" is selected from the group consisting of hydrogen and $C_1$–$C_4$ alkyl groups; and wherein R'" is selected from the group selected from hydrogen and $C_{24}$ alkyl groups, or any salts thereof.

* * * * *